(12) United States Patent
Pereira et al.

(10) Patent No.: US 9,833,615 B2
(45) Date of Patent: Dec. 5, 2017

(54) ELECTRICAL STIMULATION DEVICES AND RELATED METHODS

(71) Applicant: Boston Scientific Scimed, Inc., Maple Grove, MN (US)

(72) Inventors: Peter J. Pereira, Mendon, MA (US); David Ernest Wechter, Santa Clarita, CA (US); John M. Barker, Ventura, CA (US); Jonathan Zoll, Brookline, MA (US); Mark W. Boden, Harrisville, RI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/705,756

(22) Filed: Jun. 4, 2015

(65) Prior Publication Data
US 2016/0001067 A1 Jan. 7, 2016

Related U.S. Application Data

(60) Provisional application No. 61/989,962, filed on May 7, 2014.

(51) Int. Cl.
*A61N 1/00* (2006.01)
*A61N 1/05* (2006.01)
(Continued)

(52) U.S. Cl.
CPC .......... *A61N 1/0558* (2013.01); *A61L 24/00* (2013.01); *A61B 2017/00513* (2013.01); *A61L 24/10* (2013.01)

(58) Field of Classification Search
CPC ....... A61N 1/0558; A61L 24/00; A61L 24/10; A61B 2017/513; A61B 2017/00513
See application file for complete search history.

(56) References Cited

U.S. PATENT DOCUMENTS

| | | | | |
|---|---|---|---|---|
| 4,768,523 A | * | 9/1988 | Cahalan | A61N 1/05 516/102 |
| 5,782,898 A | * | 7/1998 | Dahl | A61N 1/057 600/374 |

(Continued)

OTHER PUBLICATIONS

Lanzafame, et al., "Laparoscopic Mesh Fixation Using Laser-Assisted Tissue Soldering in a Porcine Model," JSLS. Jul.-Sep. 2009; 13(3): 293-301.

(Continued)

*Primary Examiner* — Lindsey G Wehrheim
(74) *Attorney, Agent, or Firm* — Bookoff McAndrews, PLLC

(57) ABSTRACT

Embodiments of the present disclosure include medical apparatus, and related methods thereof. The apparatus may include a longitudinally extending lead, at least one electrode, an anchor component, and a control module. The lead may include a distal end and a proximal end. The at least one electrode may be coupled to the lead, wherein the at least one electrode may be disposed on the distal end of the lead. The anchor component may be disposed in the lead proximate of the at least one electrode. The anchor component may include solder. The control module may be operably coupled to the proximal end of the lead and may be configured to deliver energy to the at least one electrode.

13 Claims, 6 Drawing Sheets

(51) Int. Cl.
*A61L 24/00* (2006.01)
*A61B 17/00* (2006.01)
*A61L 24/10* (2006.01)

(56) References Cited

U.S. PATENT DOCUMENTS

| | | | |
|---|---|---|---|
| 6,249,708 B1 * | 6/2001 | Nelson | A61N 1/056 607/122 |
| 6,391,049 B1 * | 5/2002 | McNally | A61B 17/00491 606/214 |
| 8,224,460 B2 | 7/2012 | Schleicher et al. | |

OTHER PUBLICATIONS

Forer, et al., "Dural Defect Repair with Fascia by a $CO_2$ Laser System in a Porcine Model," Laryngoscope 116: Jun. 2006, 1002-1006.

* cited by examiner

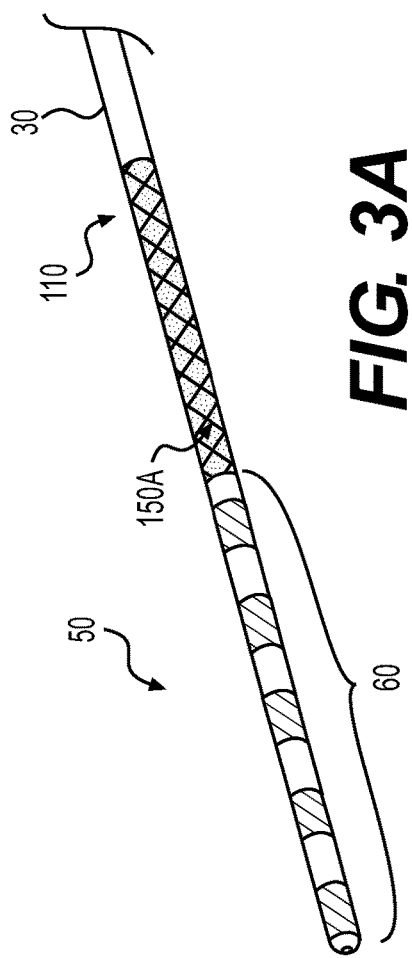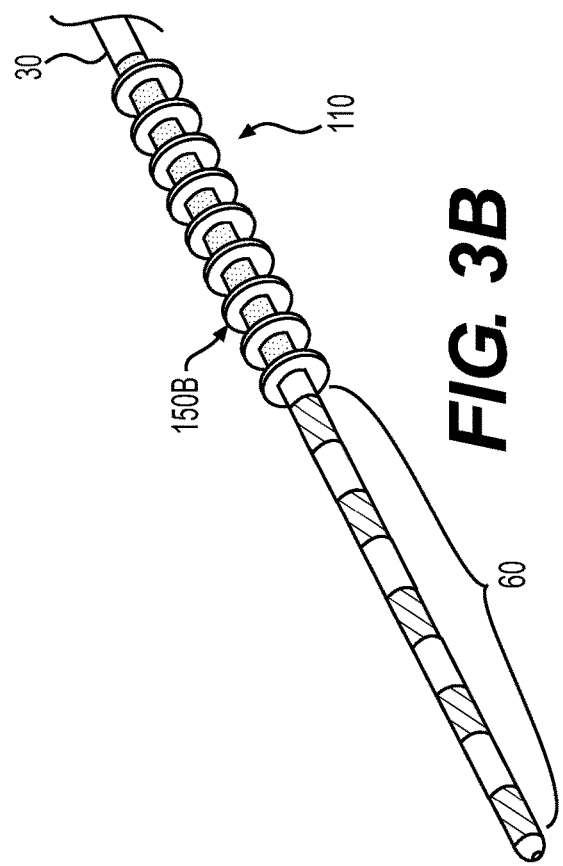

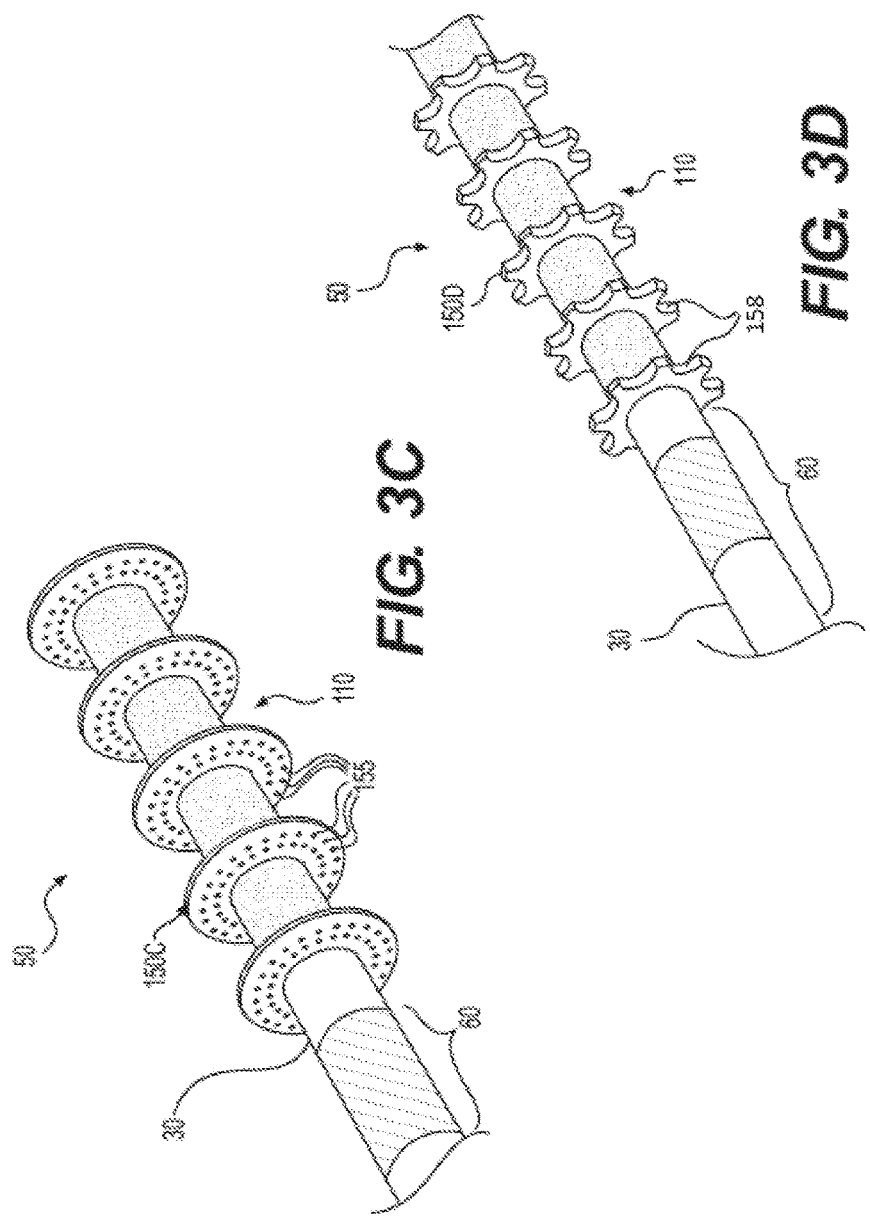

ELECTRICAL STIMULATION DEVICES AND RELATED METHODS

CROSS REFERENCE TO RELATED APPLICATIONS

This application claims the benefit of U.S. Provisional Application No. 61/989,962, filed May 7, 2014, the disclosure of which is incorporated herein by reference in its entirety.

FIELD OF THE DISCLOSURE

Embodiments of the present disclosure relate generally to medical devices and procedures. In particular, embodiments of the present disclosure relate to implantable electrical stimulation devices and related methods thereof.

BACKGROUND OF THE DISCLOSURE

Implantable neuro-stimulation systems have proven therapeutic in a wide variety of disorders e.g., Parkinson's disease, chronic neuropathic pain, or the like. For example, spinal cord stimulation systems have been used as a therapeutic modality for the treatment of chronic pain syndromes. Deep brain stimulation has also been useful for treating refractory chronic pain syndromes and has been applied to treat movement disorders and epilepsy. Peripheral nerve stimulation has been used to treat chronic pain syndrome and incontinence. Functional electrical stimulation systems have been applied to restore some functionality to paralyzed extremities in spinal cord injury patients. Additionally, sacral nerve stimulation is a promising option for patients suffering from pelvic floor disorders such as, for example, urinary incontinence, fecal incontinence, over active bladder (OAB), dual incontinence, severe constipation, or the like.

OAB is a condition often characterized by a strong urge to urinate and/or a need to urinate more often than normal. Often times, OAB occurs in patients when signals transmitted from a patient's brain to their bladder instruct the bladder to empty even when it isn't full. OAB may also occur when the muscles in a patient's bladder are too active, thereby causing more frequent evacuation. In some patients, OAB may be paired with involuntary leakage of urine from the bladder. Fecal incontinence is a condition often characterized by the inability to control bowel movements causing stool to leak unexpectedly from the rectum. In many cases, patients may suffer from both OAB and fecal incontinence, a condition referred to as dual incontinence. Patients suffering from severe constipation, including those with slow transit and others with normal transit but having impaired evacuation, often find little to no relief with conventional pharmacological and behavioral treatments.

Pelvic floor disorders may be associated with improper sacral nerve functioning which influences the operation of related organs, e.g., the bladder and large bowel (large intestine). One treatment option for such disorders is sacral nerve stimulation. Sacral nerves can be electrically stimulated to control the functioning of the bladder and/or the large bowel. The sacral nerve may be stimulated by an implantable stimulation system. The implantable sacral nerve stimulation system typically includes an implantable pulse generator and an implantable lead. The lead may include electrodes that may be positioned proximate the sacral nerve to deliver electrical pulses generated by the implantable pulse generator to the sacral nerve. However, certain challenges are associated with sacral nerve stimulation such as, for example, migration of the lead which may result in ineffective delivery of therapy.

To overcome lead migration, leads may be fixed to desired locations for stimulation. Lead fixation enables the lead to be held in place at least until the scar tissue grows around the lead. Current methods of lead fixation include the use of sutures, fixation tines, or a lead anchor device such as the "Clik Anchor" sold by Boston Scientific, Inc., or the "Cinch Anchor" or "Swift-Lock Anchor" sold by St. Jude Medical, Inc. These lead anchors, however, are too bulky to be used in Sacral Nerve Stimulation procedures. They also introduce more foreign body material into the patient resulting in an increased foreign body response and therefore increased inflammatory response. Fixation of the lead with a device or suture adds time to the operation and requires a skilled surgeon. While adhesives may be used, current implantable adhesives provide a poor or incomplete bond with low strength. Those adhesives with high fixation strength are toxic and typically only used externally. Hence, there remains a need for a lead fixation technique that is both effective, easy to deploy, and robust while causing minimal tissue damage.

SUMMARY OF THE DISCLOSURE

Embodiments of the present disclosure include an apparatus, such as, for example, an electrical stimulation system that may be used to provide electrical stimulation to tissue, e.g., nerves and methods thereof.

In one exemplary embodiment, an apparatus may include a longitudinally extending lead, at least one electrode, an anchor component, and a control module. The lead may include a distal end and a proximal end. The at least one electrode may be coupled to the lead, wherein the at least one electrode may be disposed on the distal end of the lead. The anchor component may be disposed in the lead proximate of the at least one electrode. The anchor component may include solder. The control module may be operably coupled to the proximal end of the lead and may be configured to deliver energy to the at least one electrode.

The apparatus may further include one or more of the following features: the solder may include at least one of polypeptides, nano-peptides, albumin, collagen, elastin, fibrin, fibrinogen, thrombin, prothrombin, protein derivatives, polysaccharides, or chitosan; the solder may include two or more of polypeptides, nano-peptides, albumin, collagen, elastin, fibrin, protein derivatives, polysaccharides, or chitosan; the solder may include at least one of an energy absorber, a photosensitizing dye, or a synthetic polymer; the anchor component may include a mesh; the anchor component may include at least one radial extension comprising at least one of a fin, a perforated fin, or a sectioned fin; the lead may include a central lumen extending therethrough; the apparatus may further include a longitudinally extending energy transmission element having an energy transmitter positioned at a distal end thereof, the energy transmission element may be sized for insertion through the central lumen, and the energy transmitter is configured to emit energy at a wavelength sufficient to bond the solder to tissue; the lead may be comprised of material configured to pass the wavelength of emitted energy therethrough; the at least one electrode may be an electrode array comprising between two and twelve electrodes; the electrode array may include five electrodes; each electrode of the electrode array may be electrically isolated from an adjacent electrode of the electrode array; a sheath having a lumen extending therein and an energy transmitter positioned within the lumen, the lumen may be sized to receive the lead therethrough, and wherein the energy transmitter may be configured to emit energy at a wavelength sufficient to bond the solder to tissue; the control module may include an electronic subassembly and a power source; and the sheath may include a solder lumen configured to deliver solder therethrough.

In another exemplary embodiment, a method of electrical stimulation is disclosed. The method may include delivering a longitudinally extending lead into a body of a patient, the lead may include at least one electrode and an anchor component disposed on the lead proximate of the at least one electrode and, the anchor component may include solder. The method may also include positioning a distal end of the lead such that the at least one electrode may be proximate a target tissue site. The method may further include activating an energy transmitter to emit energy therefrom, directing the emitted energy toward the solder, and bonding the lead adjacent to the target tissue site via the solder.

The method may further include one or more of the following features: the lead may include a central lumen, and directing the emitted energy toward the solder may include passing the energy transmitter within the central lumen; delivering a sheath with a central lumen over the lead, the sheath including an energy transmitter therein, and directing the emitted energy toward the solder may include positioning the energy transmitter of the sheath adjacent the solder; after the boding, transmitting electrical stimulation to the at least one electrode from a control module, and the control module may be implanted in the body of the patient; the solder may include at least one of an energy absorber, a photosensitizing dye, or a synthetic polymer; the anchor component may include a mesh, the anchor component may include at least one radial extension comprising at least one of a fin, a perforated fin, and a sectioned fin; and injecting solder through at least one solder lumen of the sheath.

In an additional exemplary embodiment, an apparatus may include a longitudinally extending lead, at least one electrode, and an anchor component. The lead may include a distal end and a proximal end. The at least one electrode may be coupled to the lead. The anchor component may be coated or embedded directly onto the lead proximate of the at least one electrode and the anchor component may include solder. The solder may include at least one of an energy absorber or a photosensitizing dye, and the solder may be configured to bond to tissue upon excitation via a bonding energy source.

The apparatus may further include one or more of following features: the bonding energy source may include at least one of a laser, a light-emitting-electrode, a radiofrequency generator, a microwave generator, a radiation generator, and a cold-plasma source; and the apparatus may further include a control module operably coupled to the proximal end of the lead, wherein the control module may be configured to deliver stimulation energy to the at least one electrode, and the control module may be configured for implantation into a body of a patient.

Additional objects and advantages of the present disclosure will be set forth in part in the description which follows, and in part will be understood from the description, or may be learned by practice of the claimed disclosure. The objects and advantages of the claimed disclosure will be realized and attained by means of the elements and combinations particularly pointed out in the appended claims.

It is to be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

FIG. 3A illustrates a schematic view of a distal end of a lead with an anchor component including mesh according to an additional embodiment of the present disclosure;

FIG. 3B illustrates a schematic view of a distal end of a lead with an anchor component including fins according to a further embodiment of the present disclosure;

FIG. 3C illustrates a schematic view of a distal end of a lead with an anchor component including perforated fins according to yet another embodiment of the present disclosure;

FIG. 3D illustrates a schematic view of a distal end of a lead with an anchor component including sectioned fins according to still another embodiment of the present disclosure;

DESCRIPTION OF THE EMBODIMENTS

Figure 1:
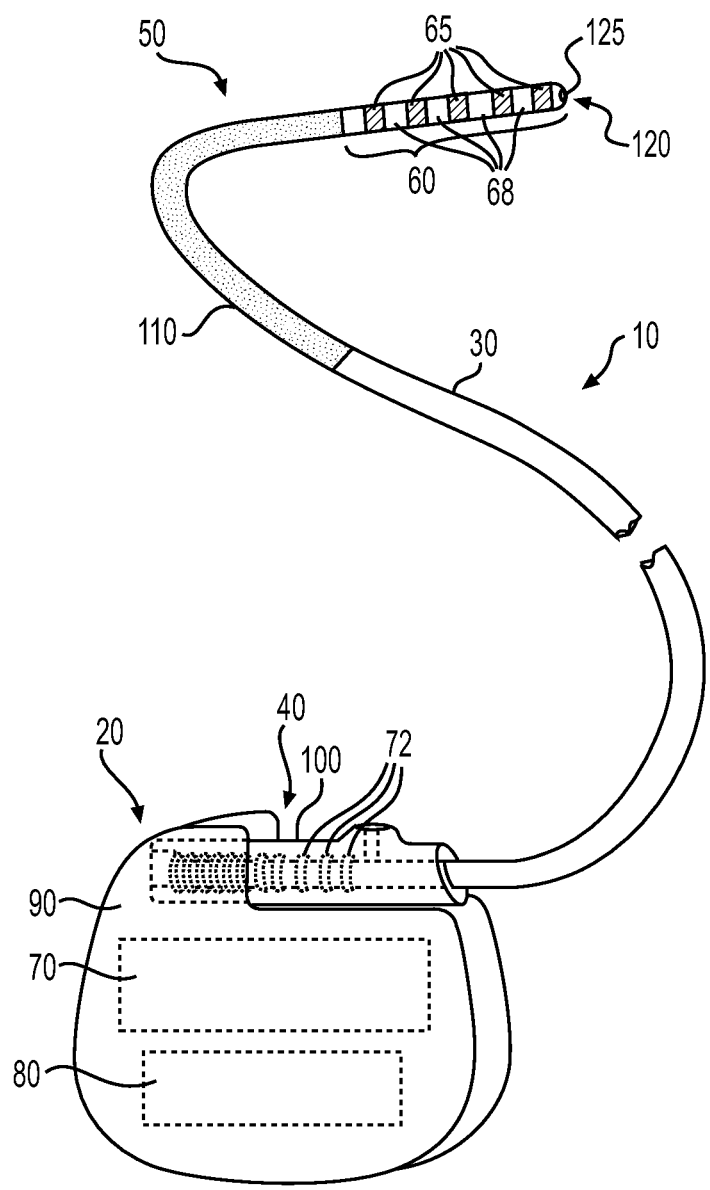
FIG. 1 illustrates an exemplary stimulation system including a lead according to the present disclosure.

Reference will now be made in detail to embodiments of the present disclosure, examples of which are illustrated in the accompanying drawings. Wherever possible, the same reference numbers will be used throughout the drawings to refer to the same or like parts. As used herein, the term "distal" refers to the direction that is away from the user and into the patient's body. By contrast, the term "proximal" refers to the direction that is closer to the user and away from the patient's body.

Overview

Embodiments of the present disclosure may include an electrical stimulation system/apparatus used to stimulate nerves, such as sacral nerves (which extend through foramina of bony structures, such as the sacra). As discussed herein, sacral nerve stimulation may be used for treating one or more different types of ailments, including fecal and/or urinary incontinence, over active bladder (OAB), severe constipation, chronic pelvis pain, and urine retention.

In the following sections, embodiments of the present disclosure will be described using sacral nerve stimulation as an exemplary treatment for pelvic floor disorders such as, for example, OAB. It will be understood, however, that this reference is merely for convenience and the devices and methods described herein may be utilized in other parts of the body and for the treatment of other ailments such as, for example, Parkinson's disease, neuropathic pain, or the like.

Exemplary Embodiments

The present disclosure includes an apparatus, e.g., an electrical stimulation system configured to stimulate a target such as a sacral nerve. The apparatus may include a longitudinally extending lead implanted adjacent the sacral nerve. Embodiments of the present disclosure include an anchor suitable for securing the lead adjacent the sacral nerve to thereby prevent inadvertent dislocation of the longitudinally extending lead relative to the target sacral nerve to which electrical stimulation is to be delivered.

In addition to the longitudinally extending lead, the electrical stimulation system may also include a control module to which a proximal end of the longitudinally extending lead may be coupled. The control module along with the lead may be implanted within the body of a patient. In particular, a distal end of the longitudinally extending lead may be implanted percutaneously adjacent the target sacral nerve, whereas the control module (which is coupled to a proximal end of the lead) may be implanted at a suitable location within the patient's body. In some embodiments, the control module may be implanted in the buttocks of the patient as is known in the art. The implantation location of the control module may be selected depending on a variety of factors including, but not limited to, (1) the length of a subcutaneous tunnel required to couple the longitudinally extending lead to the control module relative to other implantation locations, (2) whether the location impedes or prevents any inadvertent dislocation of the control module once embedded in the implantation location, etc.

Although the apparatus is employed here to electrically stimulate the sacral nerve, it should be understood that the apparatus can be used for a variety of stimulation applications including, but not limited to, brain stimulation, neural stimulation, spinal cord stimulation, muscle stimulation, or the like.

FIG. 1 illustrates an exemplary stimulation system 10 (also referred to as electrical stimulation system 10). The stimulation system 10 may include a control module 20 (e.g., an electrical stimulator or an implantable pulse generator) and a longitudinally extending lead 30 (also referred to as lead 30) coupled to the control module 20. The stimulation system 10 is configured to electrically stimulate a target nerve, muscle, and/or tissue, e.g., the sacral nerve. In some embodiments, the stimulation system 10 may include more than one lead 30 coupled to the control module 20 in order to provide therapy or deliver electrical stimulation at different locations (e.g., bilateral stimulation of Sub Thalamic Nucleus (STN) in case of Deep Brain Stimulation (DBS)).

As shown in FIG. 1, the lead 30 may include a proximal end 40, a distal end 50 and a longitudinal length extending between the proximal end 40 and the distal end 50. Thus, the lead 30 has a longitudinally extending shape and may be suited for implantation into a patient's body. In some embodiments, the lead 30 may be isodiametric along its longitudinal length. Such a lead 30 may be suitable for sacral nerve stimulation and may be deployed percutaneously through an appropriate needle or sheath, as is known in the art (e.g., Seldinger technique).

The lead 30 may include an electrode array 60 disposed along the distal end 50 of the lead 30. The electrode array 60 may include one or more electrodes 65. For example, in the illustrated embodiment, electrode array 60 includes five electrodes 65 disposed in a linear pattern along a longitudinal length of the lead 30. Typically, the electrode array 60 includes any suitable number of electrodes 65 to perform an intended treatment. Such electrodes 65 may be spaced apart such that the adjacent electrodes 65 may remain electrically isolated from one another. In some instances, an insulating member 68 may also be provided between adjacent electrodes. The insulating member 68 may be made from any one or more suitable insulating materials such as, but not limited to, silicone, polyurethane, polyvinylchloride, epoxy, or the like.

Materials employed to manufacture the electrodes 65 may include one or more suitable biocompatible materials, e.g., metals, alloys, conductive polymers, or conductive carbon, capable of conducting electrical impulses. Examples of such materials include platinum, titanium, platinum/iridium, gold, stainless steel, or a combination of these materials. In some embodiments, the electrodes 65 may be ring shaped elements disposed on the lead 30. In other embodiments, the electrodes 65 can be formed onto the lead 30 using a suitable technique such as spraying, sputtering, electroplating, metal deposition (e.g., vapor deposition, ion beam deposition), or the like. Further, any number of electrodes 65 such as, but not limited to, between two and twelve, or the like, may be used.

Further, the lead 30 may be coupled to the control module 20 through one or more terminals 72 disposed along the proximal end 40 of the lead 30 as is known in the art. The terminals 72 may be similar in shape, size, material, and number as that of the electrodes 65. The terminals 72 may electrically couple the lead 30 to the control module 20 such that the electrodes 65 may remain in electrical communication to the terminals 72.

To this end, the control module 20 may include a connector 100 including one or more electrical contacts (not shown) therein. A proximal end 40 of the lead 30 may be inserted (e.g., plugged) into the connector 100, electrically coupling the control module 20 to the lead 30. Conductor wires (not shown) may extend from the terminals 72 to the electrodes 65. Typically, one or more electrodes 65 are electrically coupled to a terminal 72. In at least one embodiment, for example, each terminal 72 is only connected to one electrode 65. The conductor wires may be embedded in the nonconductive material of the lead 30 or may be disposed in one or more lumens (not shown) extending along the lead 30. In some embodiments, there is an individual lumen for each conductor wire. In other embodiments, two or more conductor wires may extend through a single lumen. The electrical impulses generated by the control module 20 may be delivered to the electrodes 65 via the terminals 72 and thereafter, to the target, e.g., the sacral nerve.

The control module 20 may include an electronic subassembly 70 and an optional power source 80 disposed within a housing 90. The electronic subassembly 70 may include various components, e.g., a processor and processing circuitry, configured to generate electrical impulses to be delivered at the target. A processor (not shown) is generally included to control the timing and electrical characteristics of the stimulation system 10. For example, the processor can, if desired, control one or more of the timing, frequency, strength, duration, and waveform of the pulses. In addition, the processor can select which electrodes 65 can be used to provide stimulation, if desired. In some embodiments, the processor may select which electrode(s) 65 are cathodes and which electrode(s) 65 are anodes. In some embodiments, the processor may be used to identify which electrodes 65 provide the most useful stimulation of the target.

Any appropriate processor can be used. In some embodiments, the processor can be an electronic device that, for example, produces pulses at a regular interval or the processor can be capable of receiving and interpreting instructions from an external programming unit that, for example, allows modification of pulse characteristics. In some embodiments, the processor may be coupled to a receiver (not shown) which, in turn, is coupled to an optional antenna. This allows the processor to receive instructions from an external source to, for example, direct the pulse characteristics and/or the selection of electrodes 65, if desired.

In one embodiment, the antenna may be capable of receiving signals (e.g., RF signals) from an external telemetry unit (not shown) which is programmed by a programming unit (not shown). The programming unit may be external to, or part of, the telemetry unit. The telemetry unit can be a device that is worn on the skin of the user or can be carried by the user and can have a form similar to a pager, cellular phone, or remote control, if desired. As another alternative, the telemetry unit may not be worn or carried by the user but may only be available at a home station or at a clinician's office. The programming unit may be any unit that can provide information to the telemetry unit for transmission to the stimulation system 10. The programming unit can be part of the telemetry unit or can provide signals or information to the telemetry unit via a wireless or wired connection. One example of a suitable programming unit is a computer operated by the user or clinician to send signals to the telemetry unit.

The signals sent to the processor via the antenna and receiver can be used to modify or otherwise direct the operation of the stimulation system 10. For example, the signals may be used to modify the pulses of the stimulation system 10 such as modifying one or more of pulse duration, pulse frequency, pulse waveform, and pulse strength. The signals may also direct the stimulation system 10 to cease operation, to start operation, to start charging the power source 80, or to stop charging the power source 80. In other embodiments, the stimulation system 10 does not include an antenna or receiver and the processor operates only as programmed prior to or during implantation.

Optionally, the stimulation system 10 may include a transmitter (not shown) coupled to the processor and the antenna for transmitting signals back to the telemetry unit or another unit capable of receiving the signals. For example, the electrical stimulation system 10 may transmit signals indicating whether the stimulation system 10 is operating properly or not and/or indicating when the power source 80 needs to be charged or the level of charge remaining in the power source 80. The processor may also be capable of transmitting information about the pulse characteristics so that a user or clinician can determine or verify the characteristics Any power source 80 can be used including, for example, a battery such as a primary battery or a rechargeable battery. Examples of other power sources 80 include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like. As another alternative, power can be supplied by an external power source (not shown) through inductive coupling via the optional antenna or a secondary antenna (not shown). The external power source can be in a device that is mounted on the skin of the user or in a unit that is provided near the user on a permanent or periodic basis. If the power source 80 is a rechargeable battery, the battery may be recharged using the optional antenna, if desired. Power can be provided to the battery for recharging by inductively coupling the battery through the antenna to a recharging unit (not shown) external to the user. The power source 80 may be used to supply power to the electronic subassembly 70 to enable the electronic subassembly 70 to perform a predefined set of functions (e.g., to generate electrical impulses).

The stimulation system 10 may further include an anchor component 110 mounted proximate at least one electrode 65 or to the electrode array 60. The anchor component 110 may be employed to prevent migration of the lead 30 away from the target. The anchor component 110 may be coated, mounted, or otherwise embedded directly on the lead 30. In some embodiments, the anchoring component 110 may be configured to couple the lead 30 to the target nerve, muscle, or tissue surrounding the lead 30 thereby securing the lead 30 with the target. In some embodiments, the anchor component 110 may be disposed along the entire length of the lead 30 to prevent lead 30 migration. In some embodiments, the anchor component 110 may be placed within the electrode array 60 (e.g., in between two or more consecutive electrodes 65). In other embodiments, the anchor component 110 may be placed on the distal end 50 of the lead 30 e.g., distal to the electrode array 60. The anchor component 110 may include a solder configured to secure the lead 30 to the target. Solder is a material that may form a bond or union with the target to attach the lead 30 to the target. The solder may be biocompatible solder such as solders with biological origins.

In some embodiments, the thickness of the solder that may be applied to the lead 30 may range from 10 um to 2.5 mm. For example, in some embodiments the thickness of the solder may range between 100 um and 2.5 mm. The length of the solder that can be applied to the lead 30 can range from 1 mm from the proximal-most electrode 65 and continue to as far as 5 mm from the terminal 72. For example, the length of the solder applied to the lead 30 can be about 30 mm.

The anchor component 110 may be bonded to the tissue, as described in further detail below, by placing the lead 30 having anchor component 110 in close contact with a target and then applying energy from an energy transmitter (e.g., energy transmitter 140 shown in FIG. 2) to activate the anchoring component 110 thereby securing the lead 30 with the target. In this way, the lead 30 can be secured to the target without use of sutures, staples, or other fixation devices.

Figure 2:
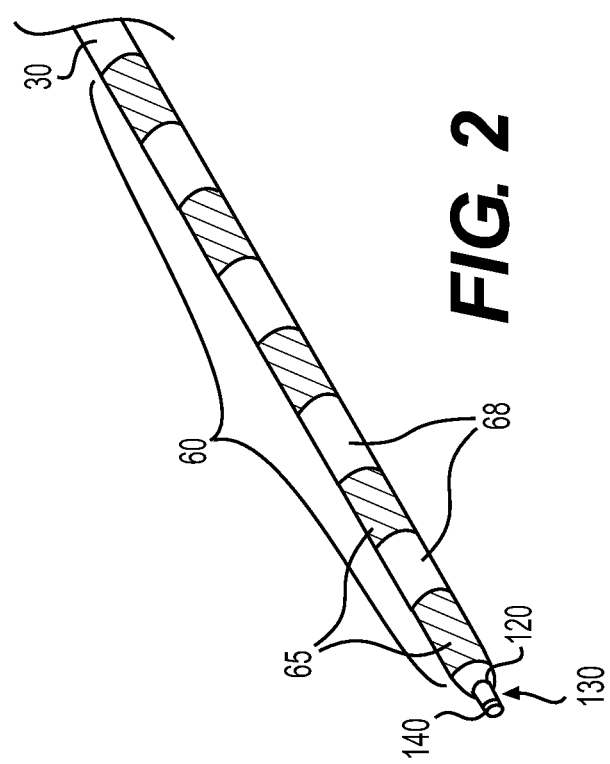
FIG. 2 illustrates a schematic view of a distal end of the lead of FIG. 1 with an exemplary energy transmitter element deployed within a central lumen of the lead according to the present disclosure.

In some embodiments, as shown in FIG. 1, the lead 30 may include a central lumen 120 configured to receive an energy transmission element (e.g., energy transmission element 130 having energy transmitter 140 disposed thereon as shown in FIG. 2). The central lumen 120 may extend along the longitudinal axis of the lead 30. The central lumen 120 may extend along an entire length of the lead 30. In such a scenario, the central lumen 120 may terminate at an opening 125 at the distal end 50 of the lead 30. In some embodiments, the central lumen 120 may extend partially along the longitudinal length of the lead 30 and terminate at a location proximal to the electrode array 60 and sufficiently close to the anchor component 110 for energizing solder. Further, the central lumen 120 may have dimensions suitable for easy insertion and advancement of the energy transmission element 130 therethrough. The central lumen 120 may receive the energy transmission element 130 for bonding the anchor component 110 to a target, e.g., the sacral nerve.

The anchor component 110 may be located on an outer surface of the lead 30 and the energy transmission element 130 may be advanced through the central lumen 120. Thereafter, energy may be transmitted through the lead 30 to the anchor component 110. Thus, the lead 30 may be formed of a wholly or partially transparent (e.g., translucent) material in order to allow energy emitted by the energy transmitter 140 on the energy transmission element 130 to reach the anchor component 110.

FIG. 2 illustrates an exemplary energy transmission element 130 disposed within the central lumen 120 of the lead 30. In some embodiments, the energy transmission element 130 may have a longitudinally extending body (e.g., rod, stylet, wire, etc.) configured to move axially relative to the lead 30 along the longitudinal length of the lead 30. The energy transmitter 140 is coupled to a distal end of the energy transmission element 130. Further, the energy transmitter 140 may be coupled to an energy source (also referred to as bonding energy source) through the energy transmission element 130. The energy transmitter 140 may be any device configured to deliver bonding energy to energize anchor component 110 as discussed in further detail below. For example, the energy transmission element 130, including the energy transmitter 140 thereon, may be pulled proximally through the central lumen 120 of the lead 30 such that, as the energy transmitter 140 passed by solder of the anchoring component 110, the anchoring component 110 may be energized. After bonding of the anchoring component 110, the energy transmission element 130 and energy transmitter 140 may be removed from the central lumen 120 and from the patient.

In some embodiments in which the anchor component 110 is placed within the electrode array 60 (e.g., in between two or more consecutive electrodes 65), the electrodes 65 themselves may be configured to activate the solder and thereby cause bonding of the lead 30 to the tissue. In such an embodiment, for example, energy transmission element 130 and/or energy transmitter 140 may be unnecessary.

The bonding energy source may be, e.g., a source of heat or light, such as a laser, a light-emitting-electrode (e.g., LEDs or OLEDs), a radiofrequency source (e.g., a microwave source), radiation sources (e.g., x-ray radiation, gamma radiation, etc.), or a locally produced plasma (e.g., cold-plasma source, argon plasma source), among others. Infrared and near-infrared laser sources include carbon dioxide ($CO_2$), thulium-holmium-chromium, holmium, thulium, and neodymium rare-earth-doped-garnets (THC:YAG, Ho:YAG, Tm:YAG, and Nd:YAG, respectively), and gallium aluminium arsenide diode (GaAlAs) lasers, among others. Visible sources include potassium-titanyl phosphate (KTP) frequency-doubled Nd:YAG, and argon lasers, among others. Argon plasmas may be used, including argon beam coagulators, which ionize argon gas to form an argon plasma and then use the plasma to deliver thermal energy to the anchor component 110. In some embodiments, an LED may be employed to activate the anchor component 110 to cause a photochemical reaction. This may prevent the surrounding tissue from overheating. In other embodiments, a laser may be used cause a thermal activation of the anchor component 110 for bonding. Gold, metal, or semiconductor nanoparticles, including rods, nanoshells, and other shapes, may be included in the anchor component 110 and heated by excitation at their plasmon frequencies.

The bonding energy source may be deployed outside the body of the patient in communication (e.g., optical or electrical) with the energy transmitter 140. For example, optical fibers and/or electrical wires may be used for communicating laser, LED, and RF (e.g., microwave) energy. In some embodiments, the bonding energy source may be a handheld energy source. Additionally, in some embodiments, the energy source may be a stand-alone unit. This may enable a single operator to handle the complete apparatus. In other embodiments, the energy transmitter 140 may draw power from the control module 20 and an additional energy source may not be required. Additionally, in some embodiments, the energy source may include a control unit, which controls the amount of energy emitting from the energy source. Preferably, the amount of energy may be sufficient to excite the anchor component 110 without significantly damaging unintended tissue. A user may provide input through the control unit (e.g., via physical buttons, touch screen, etc.) to control the energy source, thereby allowing treatment parameters to be set by a health care provider.

In some embodiments, the bonding energy source may be controlled without the use of a sensor (e.g., based on the experience of the surgeon or based on a suitable energy output algorithm). In other embodiments, a sensor (not shown) may be used in conjunction with the energy source to provide feedback regarding the amount of energy being directed to the anchor component 110 and therefore, to the target, and this feedback can be used to adjust the bonding energy source output. For example, in some embodiments, the sensor may be a temperature sensor, which detects the temperature near the anchor component 110 and prevents over-heating of adjacent tissue. Suitable software may be employed to automatically adjust the output of the energy source based on input from the temperature sensor. The sensor may be provided, for example, in the same device as the energy source or in a device that is different from the device containing the energy source.

A variety of solder materials can be used in conjunction with the present disclosure. In this regard, laser tissue soldering processes are known in the surgical art whereby tissue is bonded by applying a solder (commonly, a biological polymer) to the tissue after which a laser is used to activate the solder and form a bond. It has been reported that the mechanism of laser tissue soldering appears to include a heating-induced protein denaturation-renaturation process. See, e.g., B. Forer et al., Laryngoscope 116: June 2006, 1002-1006.

Solder materials are used in the present disclosure as an anchor to secure the lead 30 to a target, for example, by the application of heat to a solder while it is in contact with the lead 30 and the tissue, such that the lead 30 is fastened onto one or more desired locations with the tissue. As indicated above, bonding energy sources for the application of energy include radiation sources (e.g., x-ray radiation, gamma radiation, etc.), light sources (e.g., lasers, LED, etc.), radiofrequency sources (e.g., microwave sources, etc.) and plasma sources (e.g., argon beams, cold plasma etc.), among others.

Solder materials for use in conjunction with the present disclosure may include solders of biological origin and synthetic solders, which are bio-compatible. Examples of solders of biological origin include those based on biological polymers, for example, polypeptides including nano-peptides and proteins such as albumin, collagen, elastin, fibrinogen, and fibrin, protein derivatives, as well as polysaccharides including chitosan, among others. In some embodiments, two, three, four or more solder materials such as those described above are employed. Specific examples include a combination of albumin and collagen, a combination of albumin and chitosan, a combination of collagen and chitosan, and a combination of albumin, collagen, and chitosan, among many other possible combinations.

In some embodiments, the solder is mixed with synthetic polymers to improve their physical properties such as flexibility and strength. For example, Poly (lactic-co-glycolic acid) (PLGA) may be mixed with serum albumin to improve its physical properties over albumin protein solder alone.

Other polymers that might be used include water soluble or bioresorbable polymers, such as polylactic acid, polyglycolic acid, polydioxanone, polycaprolactone, tyrosine based polyesters, tyrosine based polycarbonates, polyesteramides, polyanhydrides, polyhydroxyalkanoates, polyethylene glycols, polyorthoesters, pluronics, such as block copolymers of ethylene glycol and propylene glycol, polyamides, polyvinylalcohol, hydroxyl substituted poly(meth)acrylates, polyethylene glycol substituted (meth)acrylates, (methacrylate-b-polyethers) or copolymers derived from these monomers, among others.

In some embodiments, the solder may be bio-absorbable. Over time (typically between about 4 and 60 days, depending on the solder that is used), the solder may be bio-absorbed, leaving only the lead 30 and the tissue growth behind. This may keep the lead 30 secured until the tissue growth takes place around the lead 30.

In some embodiments, the solder material may include at least one energy absorber to enhance heating efficiency and/or heat distribution within the solder material. Energy absorbers include chromophores, for example, light-specific dyes such as indocyanine green (ICG), fluorescein, basic fuchsin, and fen, nano-gold (e.g., gold nanorods, gold nanoshells, gold nanocages, etc.), SPIONs (superparamagnetic iron oxide nanoparticles), and silica nanoparticles, among other materials. Specific examples include ICG-doped albumin, fluorescein-dye-doped albumin, and nano-gold-doped albumin, among many others.

In some embodiments, photochemical tissue bonding processes take advantage of the photochemical reactions that occur at intimately associated tissue surfaces, which are stained with a photosensitizing dye (e.g., dyed tissue surfaces which are placed in contact with one another). It is believed that the dye absorbs photons of visible radiation and promotes the formation of covalent bonds between molecules on the approximated tissue surfaces. For example, reactive species that are produced upon light activation of the dye can react with potential electron donors and acceptors such as amino acids in proteins (e.g., tryptophan, tyrosine, cysteine, and so forth). In this regard, photochemical methods have been reported to form crosslinks in collagen type I molecules. See, Barbara P. Chan et al., Journal of Surgical Research 108, 77-84 (2002).

In certain aspects of the present disclosure, photosensitizing dyes may be used to secure the lead 30 to surrounding tissue, for example, by the application of light of a suitable wavelength to a photosensitizing dye and a solder material (e.g., a biological solder material, including those set forth above, among others) in intimate association with the tissue (e.g., a photosensitizing dye admixed with a solder material or coated on a surface of a solder material, in contact with and disposed on the lead 30 and in contact with the tissue), such that the lead 30 may be secured to one or more desired target locations. In some embodiments, the dye may be covalently bound to the solder or incorporated into the polymer backbone of the solder.

A light-emitting energy source such as a low-power laser or light-emitting diode (LED) may be used for this purpose, among others. In some embodiments, the solder material may include at least one photosensitizing dye to enhance absorption of light and enhance excitation process of solder material. Examples of photosensitizing dyes include, for example, indocyanine green, gold nanoparticles, and SPIONs (superparamagnetic iron oxide nanoparticles), or the like. Other examples of photosensitizing dyes include xanthene dyes such as rose bengal, methylene blue and fluorescein, riboflavin dye (e.g., riboflavin-5-phosphate), lumichrome dye, lumiflavin dye, Reactive Black 5, thiazine dye, erythrosine, N-hydroxypyridine-2-(1H)-thione (N-HTP), protoporphyrin I through protoporphyrin IX, coproporphyrins, uroporphyrins, mesoporphyrins, hematoporphyrins and sapphyrins, chlorophylis, e.g., bacteriochlorophyll A, Photofrin®, synthetic diporphyrins and dichlorins, phthalocyanines with or without metal substituents, chloroaluminum phthalocyanine with or without varying substituents, O-substituted tetraphenyl porphyrins, 3,1-meso tetrakis (o-propionamido phenyl) porphyrin, verdins, purpurins, tin and zinc derivatives of octaethylpurpurin, etiopurpurin, hydroporphyrins, bacteriochlorins of the tetra(hydroxyphenyl) porphyrin series (e.g., protoporphyrin I through protoporphyrin IX, coproporphyrins, uroporphyrins, mesoporphyrins, hematoporphyrins and sapphyrins), chlorins, chlorine6, mono-1-aspartyl derivative of chlorin e6, di-1-aspartyl derivative of chlorin e6, tin(IV) chlorin e6, meta-tetrahydroxphenylchlorin, benzoporphyrin derivatives, benzoporphyrin monoacid derivatives, tetracyanoethylene adducts of benzoporphyrin, dimethyl acetylenedicarboxylate adducts of benzoporphyrin, Diels-Adler adducts, monoacid ring "a" derivative of benzoporphyrin, sulfonated aluminum PC, sulfonated AlPc, disulfonated, tetrasulfonated derivative, sulfonated aluminum naphthalocyanines, naphthalocyanines with or without metal substituents and with or without varying substituents, chlorophylis, bacteriochlorophyll A, anthracenediones, anthrapyrazoles, aminoanthraquinone, phenoxazine dyes, phenothiazine derivatives, chalcogenapyrylium dyes, cationic selena and tellurapyrylium derivatives, ring-substituted cationic PC, pheophorbide derivative, naturally occurring porphyrins, hematoporphyrin, ALA-induced protoporphyrin IX, endogenous metabolic precursors, 5-aminolevulinic acid, benzonaphthoporphyrazines, cationic imminium salts, tetracyclines, lutetium texaphyrin, texaphyrin, tin-etio-purpurin, porphycenes, benzophenothiazinium, eosin, erythrosin, cyanines, merocyanine 540, selenium substituted cyanines, flavins, riboflavin, proflavin, quinones, anthraquinones, benzoquinones, naphthaldiimides, naphthalimides, victoria blue, toluidine blue, dianthroquinones (e.g., hypericin), fullerenes, rhodamines and photosensitive derivatives thereof.

In some embodiments, as shown in FIGS. 3A-3D, anchor component 110 may be designed (e.g., configured, provided, include, etc.) with increased surface area so as to support additional solder of anchoring component 110 to improve the bond between lead 30 and the target. That is, one or more of the lead 30 and anchor component 110 may further include a three-dimensional structure comprising voids or pores on and/or through which additional solder may be disposed. FIG. 3A, for example, illustrates the distal end 50 of lead 30 including a mesh (or mesh component) 150A. The mesh 150A may increase the surface area of the anchor component 110 in contact with tissue and may include increased surfaces containing solder to improve bonding with tissue. The mesh 150A may also facilitate tissue ingrowth. In some embodiments, the mesh 150A may form an integral component with the lead 30 whereas, in other embodiments, the mesh 150A may be separately formed and disposed onto the lead 30. In some embodiments, the mesh 150A may be formed of the solder and disposed onto the lead 30.

In some embodiments, the mesh 150A may include a number of filaments or strands, which are woven, knitted, entwined, and/or braided together. The mesh 150A may form a web-like structure. The mesh 150A may be a regular mesh with uniform arrangement of pores or an irregular mesh with non-uniform arrangement of pores. In some embodiments, the mesh 150A may have a predetermined arrangement or pattern, for example, a layered, clustered matrix, honeycomb, or other arrangement.

The mesh 150A may be formed using a suitable biocompatible material such as, but not limited to, PMMA (Poly (methyl methacrylate)), polyethylene, polypropylene, nylon, PEEK, terylene, silicone, polyurethane, plastic Dacron™, stainless steel, titanium, platinum, gold, silver, any suitable alloy, or the like. Additionally, in some embodiments, the mesh 150A may be formed of an adhesive, heat bonding material, pressure bonding material, or the like. Any biocompatible adhesive may be used, including, but not limited to, epoxy resins, acrylic resins, polyurethane adhesives, colloidal epoxy silica, or the like. The mesh may be bioresorbable or biostable.

Further, in some embodiments, the anchor component 110 may include one or more radial extensions disposed along the anchor component 110 to increase the surface area of the anchor component 110. For example, FIG. 3B illustrates the distal end 50 of the lead 30 including fins 150B. As shown, the fins 150B may be disc-like components radiating outwards relative to a longitudinal axis of the lead 30. As shown, the fins 150B may be solid. In other embodiments, as shown in FIG. 3C, perforated fins 150C may be utilized. The perforations 155 may further increase the surface area of the anchor component 110 and also the amount of solder that can be coated onto the lead 30. The perforations 155 may also enable tissue growth therethrough, thereby securing the lead 30 with the tissue. While perforations 155 are shown arranged in two concentric circles about each fin 150C, perforations 155 may be arranged in any manner, whether symmetric, asymmetric, or irregular. Additionally, in some embodiments, perforations 155 may be only disposed through some rather than all fins 150C. In additional embodiments, as shown in FIG. 3D, the anchor component 110 may include sectioned fins 150D (e.g., gear-shaped fins) with grooves 158. The grooves 158 may provide additional surface over which the solder can be disposed. Additionally, in some embodiments, grooves 158 may be only disposed along some rather than all fins 150D. It is understood that any appropriate number, spacing, and dimensions of fins 150B-C may be utilized to promote tissue ingrowth and improve the bonding of the anchor component to the target. Additionally, any appropriate method of manufacture, e.g., molding, piercing, stamping, extruding, or the like may be used to manufacture mesh 150A or fins 150B-D. Additionally, any combination of mesh 150A and fins 150B-D may be employed. For example, in some embodiments, anchor component 110 may include a combination of mesh 150A and one or more of fins 150B-D.

In some embodiments, a lead 30 may be provided with one or more non-woven fiber coatings (not shown) via an electrospinning technique. Such non-woven fiber coatings may promote tissue ingrowth and may utilize either synthetic or biological materials. For example, in some embodiments, a non-woven fiber coating may comprise isobutylene-styrene copolymers (e.g., SIBS), polyurethanes, polyamides, polyalkanes, polyalkenes, polyethylene glycol, polypropylene glycols, polyesters, polyacrylates, polymethacrylates, polyvinyl alcohols, polyvinyl ethers, polycarbonates, polyanhydrides, styrenic polymers, biopolymers such as polytyrosines, peptides, collagen, cellulosics, carbohydrates and copolymers of the above, among others. In some embodiments, for example, these polymers may be biodegradable. The selected fiber diameter and pore size may be adjusted to optimize adhesion and tissue in-growth. For example, pore sizes of 1 to 1000 um are desirable, 50-100 um are optimized for adventitia ingrowth. Fiber diameters can range from 50 nm to 1000 um, with optimum sizes from 15-20 um.

Figure 4:
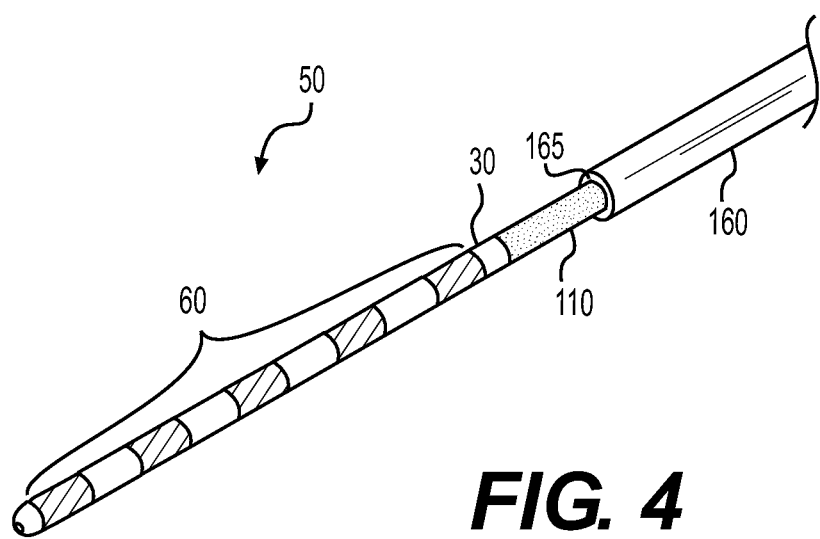
FIG. 4 illustrates a schematic view of a distal end of a lead and a sheath including an energy transmitter within according to another embodiment of the present disclosure.

In other embodiments, a roughened surface may be desirable for enhanced adhesion between the anchor component 110 and the electrodes. This surface may be generated during formation of the lead. Examples include addition of micronized silica particles to the lead body. The particles can be from 100 nm to 1000 um in diameter, with optimal size being in the range from 1-10 um. Additionally, the lead can be formed with other surface features, including grooves, wells, raised segments, such as pins, walls, hemispheres, among others, to provide a physical attachment point for the anchor component 110. These features may range from 10 nm to 1000 um, with optimized sizes from 1-10 um. In some embodiments, a sheath may be employed over the lead 30 for energizing solder. For example, FIG. 4 illustrates the distal end 50 of the lead 30 with a sheath 160. Similar to the embodiment of FIG. 2, the lead 30 may include the electrode array 60 and the anchor component 110. To activate the anchor component 110, energy may be delivered through the sheath 160 disposed over the lead 30. In such embodiments, lead 30 may or may not include lumen 120 and/or opening 125. The sheath 160 may be a longitudinally extending member having a distal end, a proximal end, and a lumen 165. The lumen 165 may extend longitudinally along a length of the sheath 160 from the proximal end to the distal end. The lumen 165 may be configured to receive the lead 30 such that the sheath 160 can be advanced or retracted over the distal end of the lead 30. The lumen 165 may have an interior surface. The interior surface of the lumen 165 may include an energy transmitter 140 (not shown in FIG. 4) at the distal end of the sheath 160. The energy transmitter 140 may be similar to the energy transmitter 140 shown in FIG. 2 and may be configured to bond the lead 30 via the solder. Once the anchor component 110 is excited, the lead 30 may bond to the target and the sheath 160 can be removed leaving the lead 30 in place.

In some embodiments, the sheath 160 may include one or more lumens configured to carry conductors or fibers to deliver energy to the energy transmitter. In other embodiments, the conductors or fibers may be embedded within the sheath 160 during manufacturing. The sheath 160 may be formed using flexible biocompatible materials such as, for example, polymers, metals, metal alloys, and metal-polymer composites. In some embodiments, sheath 160 may include one or more lumens for delivery of liquid solder therethrough. In such cases, anchor component 110 need not be located on the lead prior to positioning adjacent a target. Rather, after positioning of a lead lacking (e.g., free from, not including, etc.) an anchoring component 110 adjacent a target, liquid solder of an anchoring component 110 may be injected through one or more lumens of sheath 160. Energy transmitter 140 of sheath 160 may be configured to simultaneously excite the solder during injection such that the anchoring component is activated to promote bonding. That is, in some embodiments, disposition of solder of an anchoring component 110 on the lead 30 may be performed at the same time and in conjunction with excitation of the injected solder of the anchoring component 110. Such an embodiment may prevent contamination of the anchoring component 110 prior to fixation of the lead 30 to the target. In some arrangements, the one or more lumens for delivery of liquid solder may terminate at a distal side port (not shown) of sheath 160.

In some embodiments, the sheath 160 may include one or more coatings. For example, a suitable low-friction material, such as TEFLON®, polyetheretherketone (PEEK), polyimide, nylon, polyethylene, hydrogel based coatings such as those known in the art, including HydroGlide, Biocoat, Lubrilast, and Baymedix CL 100, among others, and/or other lubricious polymer coatings may be applied to the interior surface of the lumen to facilitate insertion of the lead 30 into the body.

In other embodiments, the lead 30 may include anchor component 110 including a material that may become tacky when it comes in contact or is exposed to the tissue. Hence, at least the anchor component 110 of the lead 30 may remain covered by the sheath during implantation. Once the lead 30 reaches a target location, the sheath 160 may be removed exposing the anchor component 110 to the tissue. Then the anchor component 110 may become tacky and may adhere to the tissue in contact. The tackiness of the anchor component 110 may be sufficient enough to secure the lead 30 in place until tissue grows around the lead 30. Accordingly, in such a scenario, sheath 160 may not be required to include an energy transmitter 140.

In other embodiments, bidirectional barbs (not shown) may be utilized to prevent lead 30 migration. For example, barbs may be coupled to the lead 30 and contained within sheath 160 (FIG. 4). These barbs would be constrained by the sheath 160 and spring open when the sheath 160 is removed, thereby engaging the tissue. These barbs could be degradable, remaining in the body for 14 days to 2 years to up to 4 years. Optimal duration would be 3 months to allow healing and tissue ingrowth that would anchor the lead 30. The barbs could be made from any biostable or biodegradable material, including metals or polymers, among others. The barbs should extent out from the lead 30 at opposing angles to prevent movement in any direction. The barbs could be from 1 um to 5 mm long, with the optimum length being 1 mm. Additionally or alternatively, such barbs may be comprised of shape memory polymer that is either biodegradable or biostable. Examples of shape memory polymers that have a triggering temperature at or below 37 C include POSS polyurethanes with PLGA and polyethylene glycol soft segments, such as those described in Knight et al. Journal of Biomedical Materials Research Part A. 2010 August; 94(2):333-43. Examples of biostable shape memory polymers include polycyclooctenes, such as those described in Mather, et al., Macromolecules 2002, 35, 9868-9874.

Figure 5:
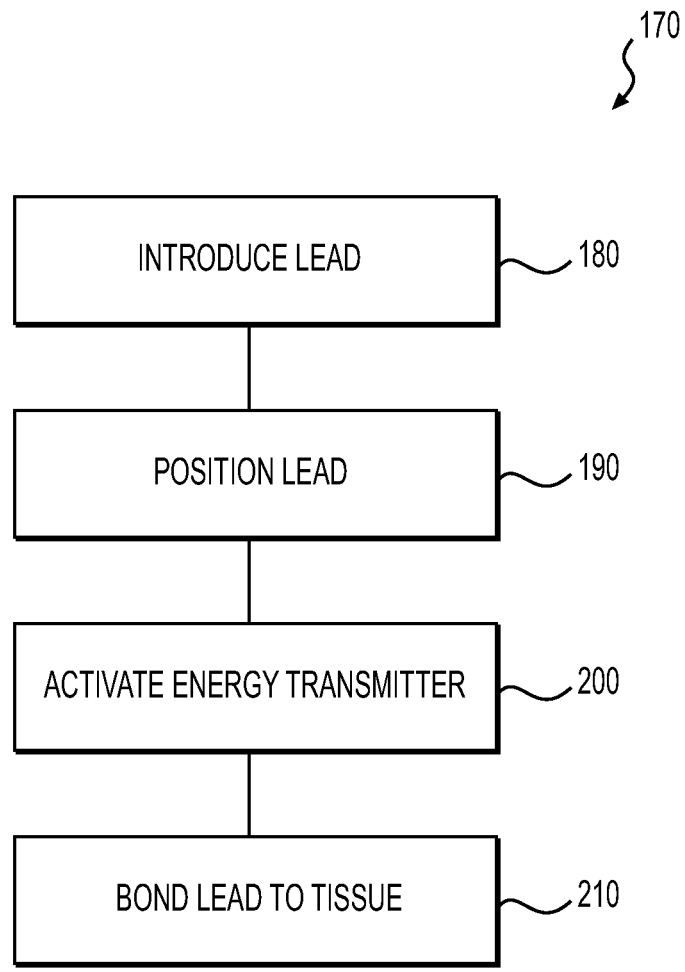
FIG. 5 illustrates a schematic view an exemplary method of use of an electrical stimulation system according to an embodiment of the present disclosure.

As noted above, pelvic floor disorders such as, for example, OAB, fecal incontinence, and severe constipation may be treated via sacral nerve stimulation by sending electrical pulses to the sacral nerve which may influence the bladder and other muscles to manage urinary and bowel function. Electrical pulses may be delivered to sacral nerve through lead 30. FIG. 5 describes an exemplary method 170 for implanting and securing the lead 30 within the body of a patient according to the present disclosure. A needle (e.g., a 20 gauge needle) may be inserted parallel to sacral nerve (e.g., by puncturing the skin), typically into the S3 foramen under fluoroscopic guidance. The needle may include a stylet slidably disposed within a lumen of the needle. The stylet may be configured to reside in the needle during insertion. Then, stimulation may be applied to confirm position of the needle. For example, the physician may check for desired responses such as bellows movement, flexion of great toe, dystonia of foot muscles. In some embodiments, the patient may be asked to confirm responses such as sensations in the anus, perineum, vagina, and/or scrotum. Once the position of the needle is confirmed, the stylet may be removed. Removal of the stylet may create a space within the needle to receive a guide wire. Then, the guide wire may be inserted through the needle. Once, the guide wire is sufficiently advanced to reach a target location, the needle may be removed.

Then, a small incision (e.g., 2 inches) may be made on either side of the guide wire to insert an introducer (e.g., introducer sheath) to be advanced over the guide wire. Once the introducer is suitably placed, the guide wire is removed. In some arrangements, the introducer may also include a dilator configured to be inflated so as to fill an annular space between the guide wire and an inside circumferential surface of the introducer sheath. Next the lead 30 may be introduced (step 180) into the body of the patient via the introducer. The lead 30 is positioned (step 190) and is connected to a temporary external stimulator. Stimulation may be applied to confirm the position of the lead. Once the position of the lead is confirmed, an energy transmitter 140 is activated (step 200) to excite an anchor component 110 disposed on the lead 30. The energy transmitter 140 may include an LED, for example, and the anchor component 110 may include a solder. The LED source may produce light that may be directed towards the solder. For example, the energy transmitter 140 may be pulled proximally relative to the lead 30 so as to pass the solder of the anchoring component 110. Directing the light towards the solder may excite the solder and may cause bonding of the lead 30 to the target tissue (step 210).

One advantage of using light (LED), rather than heat, to achieve lead-to-tissue bonding is that complications due to uneven heat distribution can be reduced or eliminated. Another advantage of using light rather than heat is that there is less risk of causing damage to the tissue (e.g., cell death). In addition, the use of wavelength-specific absorbers such as chromophores enables differential absorption between the chromophore-containing regions and surrounding tissue. One advantage is a selective absorption of radiation by the target, without the need for a precise focusing. Moreover, lower power levels may be used because of the increased absorption of chromophore-containing regions, leading to reduced tissue damage.

Further, after bonding of the lead 30, a pocket may be created in the subcutaneous fat, typically in the upper buttock of the patient using dissection and electro-cautery to place the control module 20. The control module may generate electrical pulses to be delivered to the sacral nerve. The control module 20 may be placed below and parallel to the skin. In some embodiments, the control module 20 may be placed less than, for example, 2.5 cm. The pulses generated by the control module 20 may be delivered via the lead 30. To connect the lead 30 with the control module 20, a tunnel may be created from the lead incision to the pocket for the control module 20 using a tunneling tool. The tunneling tool is then utilized to thread the proximal end of the lead 30 through the tunnel. The lead 30 is then coupled to the control module 20 and then the control module 20 is placed in the pocket. Once the control module 20 is placed within the pocket, the pocket may be closed using sutures as is known in the art. Prior to suturing, the pocket may be flushed with antibiotic solution such as betadine to avoid, prevent, or resist any infection.

In some embodiments, the stimulation system/apparatus (such as stimulation system 10) may be provided as a kit to the patient or medical professional. The kit may include a control module 20 (e.g., pulse generator), one or more leads 10 with or without anchoring component 110, an introducer (for delivery of the lead 30), and printed material with storage and/or implantation instructions.

Other embodiments of the present disclosure will be apparent to those skilled in the art after consideration of the specification and practice of the embodiments disclosed herein. It is intended that the specification and examples be considered as exemplary only, with a true scope and spirit of the disclosure being indicated by the following claims.

Although the present disclosure is described with reference to electrical stimulation of the sacral nerve, it is understood that the present disclosure may also be used in other forms of minimally invasive surgery or percutaneous therapeutic surgery.

The invention claimed is:

1. An apparatus, including:
a longitudinally extending lead having a distal end, a proximal end, and a central lumen extending therethrough;
at least one electrode coupled to the lead, wherein the at least one electrode is disposed on the distal end of the lead;
an anchor component disposed on the lead between the proximal end and the at least one electrode, the anchor component comprising solder;
a control module operably coupled to the proximal end of the lead, the control module being configured to deliver energy to the at least one electrode, and
a longitudinally extending energy transmission element having an energy transmitter positioned at a distal end thereof, the energy transmission element sized for insertion through the central lumen, and wherein the energy transmitter is configured to emit energy to bond the solder to tissue.

2. The apparatus of claim 1, wherein the solder includes at least one of polypeptides, nano-peptides, albumin, collagen, elastin, fibrin, protein derivatives, polysaccharides, or chitosan.

3. The apparatus of claim 1, wherein the solder includes two or more of polypeptides, nano-peptides, albumin, collagen, elastin, fibrin, protein derivatives, polysaccharides, or chitosan.

4. The apparatus of claim 1, wherein the solder includes at least one of an energy absorber, a photosensitizing dye, or a synthetic polymer.

5. The apparatus of claim 1, wherein the anchor component includes a mesh formed of the solder.

6. The apparatus of claim 1, wherein the anchor component includes at least one radial extension comprising at least one of a fin, a perforated fin, or a sectioned fin.

7. The apparatus of claim 1, wherein the lead is comprised of material configured to pass the emitted energy therethrough.

8. The apparatus of claim 1, wherein the at least one electrode is an electrode array comprising between two and twelve electrodes.

9. The apparatus of claim 1, wherein the anchor component is longitudinally disposed on the lead.

10. The apparatus of claim 9, wherein the anchor component extends over at least a portion of the distal end of the lead.

11. The apparatus of claim 1, wherein the anchor component is coated onto the lead.

12. The apparatus of claim 1, wherein the anchor component is embedded directly into the lead.

13. The apparatus of claim 1, wherein the anchor component is coated or embedded directly onto the lead proximal to the at least one electrode.

* * * * *